(12) United States Patent
Mitsumori

(10) Patent No.: US 11,676,720 B2
(45) Date of Patent: Jun. 13, 2023

(54) MEDICAL INFORMATION PROCESSING APPARATUS

(71) Applicant: CANON MEDICAL SYSTEMS CORPORATION, Otawara (JP)

(72) Inventor: Keita Mitsumori, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 367 days.

(21) Appl. No.: 16/872,686

(22) Filed: May 12, 2020

(65) Prior Publication Data
US 2020/0365273 A1    Nov. 19, 2020

(30) Foreign Application Priority Data

May 17, 2019   (JP) .............................. JP2019-093652

(51) Int. Cl.
*G16H 50/20*   (2018.01)
*G16H 50/30*   (2018.01)
(Continued)

(52) U.S. Cl.
CPC ............. *G16H 50/20* (2018.01); *G16H 10/60* (2018.01); *G16H 50/30* (2018.01); *G16H 50/70* (2018.01)

(58) Field of Classification Search
CPC combination set(s) only.
See application file for complete search history.

(56) References Cited

U.S. PATENT DOCUMENTS

| | | | |
|---|---|---|---|
| 6,988,075 B1 * | 1/2006 | Hacker .................. | G16H 10/60 705/2 |
| 2002/0188467 A1 * | 12/2002 | Eke ........................ | G16H 40/67 705/2 |

(Continued)

FOREIGN PATENT DOCUMENTS

| | | |
|---|---|---|
| JP | 2001-118014 A | 4/2001 |
| JP | 2005-209186 A | 8/2005 |

OTHER PUBLICATIONS

Oviawe, E. (2018). Design and development of simulation-based instruction on meaningful use and interprofessionalism core competencies in a healthcare team-based learning environment (Order No. 10936884). Available from ProQuest Dissertations and Theses Professional. (2124444083). (Year: 2018).*

(Continued)

*Primary Examiner* — Amber A Misiaszek
(74) *Attorney, Agent, or Firm* — Oblon, McClelland, Maier & Neustadt, L.L.P.

(57) ABSTRACT

A medical information processing apparatus according to an embodiment includes processing circuitry and a hardware display device. The processing circuitry generates a plurality of sets of virtual patient information in each of which patient attribute information, at least one medical action, at least one medical event, and at least one test result are associated with one another; receives a user's operation of selecting one of the sets of virtual patient information; and causes the hardware display device to display the event and the medical action included in the selected piece of virtual patient information in time series. The hardware display device displays, under control of the processing circuitry, the event and the medical action included in the selected piece of virtual patient information in time series.

10 Claims, 13 Drawing Sheets

(51) Int. Cl.
*G16H 50/70* (2018.01)
*G16H 10/60* (2018.01)

(56) References Cited

U.S. PATENT DOCUMENTS

| | | | | |
|---|---|---|---|---|
| 2005/0170323 | A1* | 8/2005 | Jarrell | G09B 23/28 434/262 |
| 2007/0061393 | A1* | 3/2007 | Moore | H04L 67/02 709/201 |
| 2008/0015418 | A1* | 1/2008 | Jarrell | G16H 70/20 600/300 |
| 2008/0288293 | A1* | 11/2008 | Brown, Jr. | G16H 20/10 705/2 |
| 2014/0113263 | A1* | 4/2014 | Jarrell | G09B 23/28 434/262 |
| 2020/0286294 | A1* | 9/2020 | Musara | G16H 50/30 |

OTHER PUBLICATIONS

Office Action issued Apr. 25, 2023 in Japanese Patent Application No. 2019-093652, citing reference no. 15 therein.

* cited by examiner

FIG.4

| VIRTUAL PATIENT ID | INJURY/ DISEASE NAME | CONDITION ON ENTERING HOSPITAL | GENDER | AGE | FINAL EVENT | ADVANCED MEDICAL CARE |
|---|---|---|---|---|---|---|
| V00001 | BILE DUCT INFLAMMATION | ... | MALE | THIRTIES | HOSPITAL DISCHARGE | NOT APPLIED |
| V00002 | LUNG CANCER | STAGE 2 | MALE | THIRTIES | HOSPITAL DISCHARGE | NOT APPLIED |
| V00003 | LUNG CANCER | STAGE 4 | FEMALE | SEVENTIES | DEATH | NOT APPLIED |
| V00004 | LUNG CANCER | STAGE 4 | FEMALE | SEVENTIES | HOSPITAL DISCHARGE | APPLIED |
| V00005 | FEMORAL FRACTURE | ... | - | TEENS | HOSPITAL DISCHARGE | NOT APPLIED |
| V00006 | FEMORAL FRACTURE | ... | - | SEVENTIES | HOSPITAL DISCHARGE | NOT APPLIED |
| ⋮ | ⋮ | ⋮ | ⋮ | ⋮ | ⋮ | ⋮ |

50

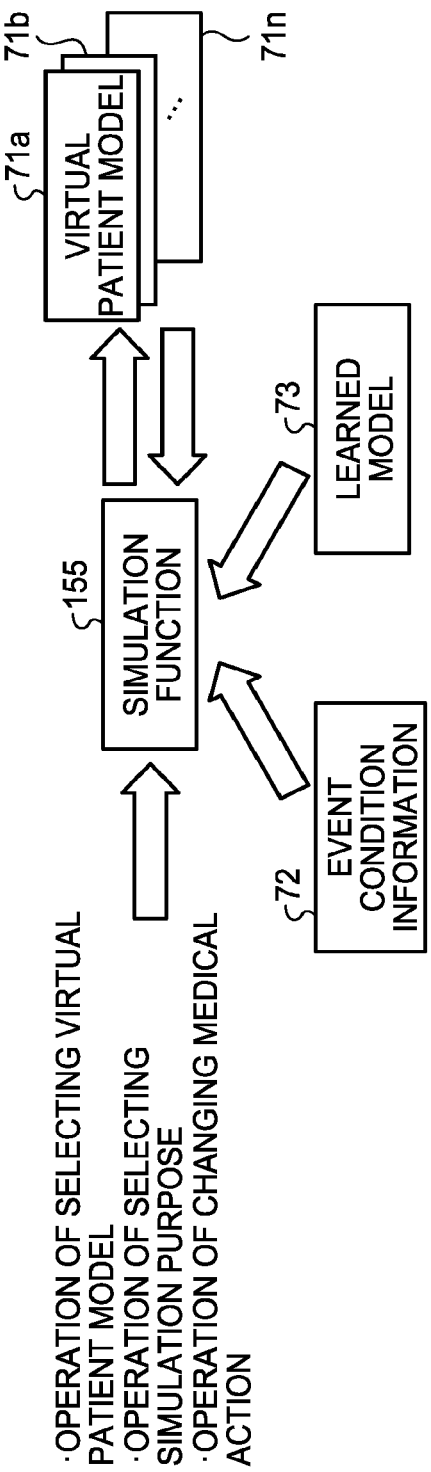

MEDICAL INFORMATION PROCESSING APPARATUS

CROSS-REFERENCE TO RELATED APPLICATIONS

This application is based upon and claims the benefit of priority from Japanese Patent Application No. 2019-093652, filed on May 17, 2019; the entire contents of which are incorporated herein by reference.

FIELD

Embodiments described herein relate generally to a medical information processing apparatus.

BACKGROUND

A conventionally known technique accumulates information regarding past medical treatment records and enables a doctor and others to search the information according to intended use. Another known technique presents a medical action recommended for a specific patient based on past medical treatment records.

It is difficult for a doctor and others to examine or improve a past process of a patient up to the final medical event, based on past medical information in a medical institution.

BRIEF DESCRIPTION OF THE DRAWINGS

FIG. 4 is a view illustrating an example of an initial display screen according to the first embodiment;

FIG. 7 is a view for explaining processing of a simulation function according to the first embodiment;

DETAILED DESCRIPTION

Embodiments of a medical information processing apparatus will be described below with reference to the drawings.

First Embodiment

A medical information processing apparatus according to an embodiment includes processing circuitry and a hardware display device. The processing circuitry generates a plurality of sets of virtual patient information in each of which patient attribute information, at least one medical action, at least one medical event, and at least one test result are associated with one another; receives a user's operation of selecting one of the sets of virtual patient information; and causes the hardware display device to display the event and the medical action included in the selected piece of virtual patient information in time series. The hardware display device displays, under control of the processing circuitry, the event and the medical action included in the selected piece of virtual patient information in time series.

Figure 1:
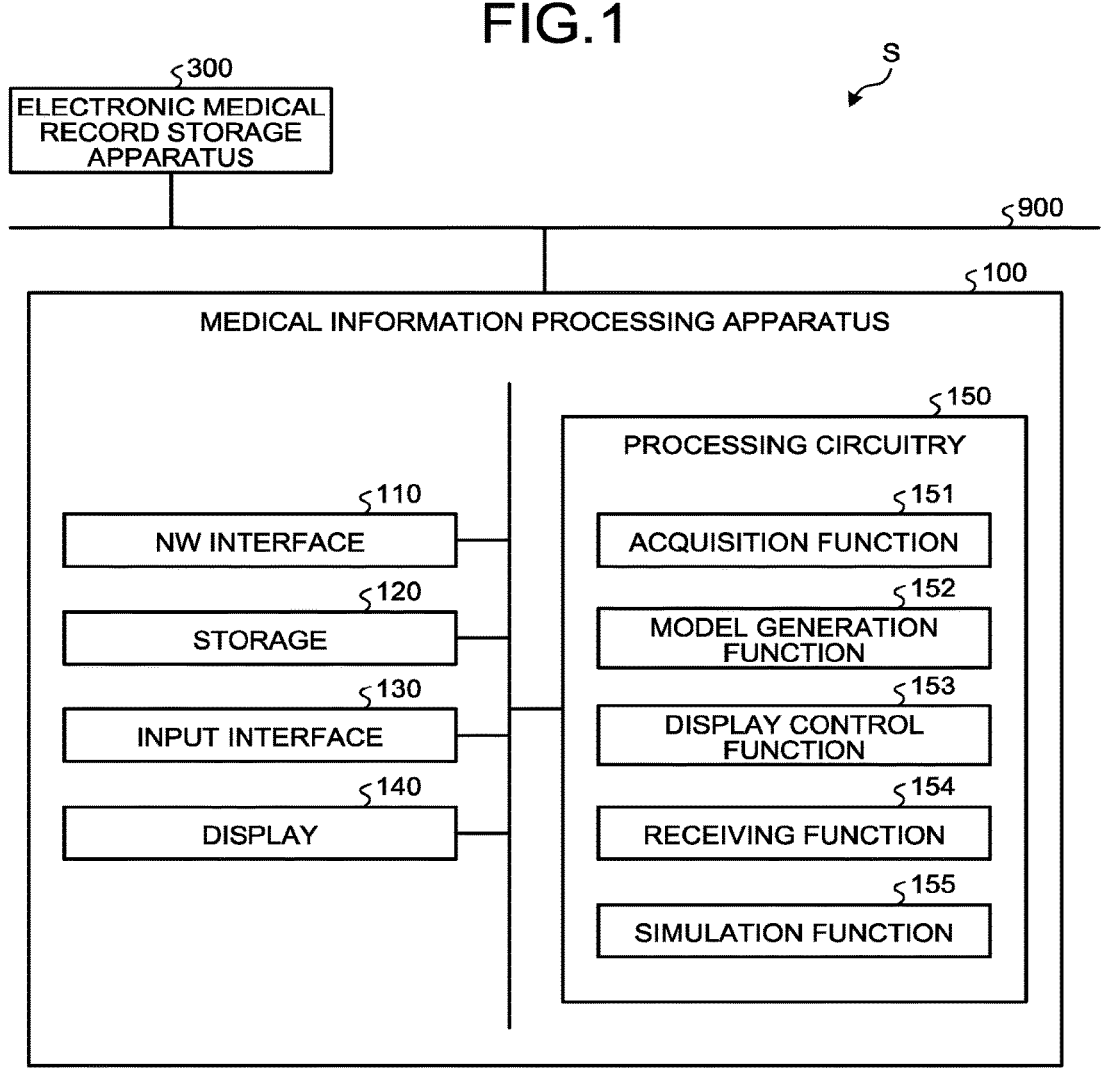
FIG. 1 is a block diagram illustrating a configuration example of a medical information processing system according to a first embodiment.

FIG. 1 is a block diagram illustrating a configuration example of a medical information processing system S according to a first embodiment. As illustrated in FIG. 1, the medical information processing system S includes a medical information processing apparatus 100, and an electronic medical record storage apparatus 300. The medical information processing apparatus 100 and the electronic medical record storage apparatus 300 are connected via a network 900. The network 900 is, for example, a hospital local area network (LAN) or the Internet.

The electronic medical record storage apparatus 300 stores medical data regarding various medical treatments performed in a hospital and other facilities. For example, the electronic medical record storage apparatus 300 is installed as a part of an electronic medical record system introduced in the hospital and other facilities so as to store medical data generated by the electronic medical record system. For example, the electronic medical record storage apparatus 300 is achieved by computer equipment such as a database (DB) server, and stores the medical data in a storage such as a semiconductor memory including a random-access memory (RAM) and a flash memory, a hard disk, and an optical disk.

The medical data regarding various medical treatments stored in the electronic medical record storage apparatus 300 includes information indicating past medical treatment records, and is also referred to as medical record information. The detailed contents of the medical record information will be described later.

The medical information processing apparatus 100 is, for example, a computer such as a personal computer (PC). To be more specific, the medical information processing apparatus 100 includes a network (NW) interface 110, a storage 120, an input interface 130, a display 140, and processing circuitry 150.

The NW interface 110 is connected to the processing circuitry 150 so as to control transmission of various data and communication between the medical information processing apparatus 100 and the electronic medical record storage apparatus 300. The NW interface 110 is achieved by, for example, a network card, a network adapter, or a network interface controller (NIC).

The storage 120 is connected to the processing circuitry 150 so as to store various information used in the processing circuitry 150 in advance. In the present embodiment, the storage 120 stores guidelines, the medical record information, virtual patient models, event condition information, and a learned model.

The guidelines in the present embodiment include medical guidelines applied to medical treatments in a medical institution where the medical information processing apparatus 100 is used, and ethical guidelines. Examples of the guidelines include rules such as upper limits of medicine doses and patient conditions for each of various types of surgery. The guidelines also follow various regulations concerning medical services established by the country.

The medical record information, the virtual patient models, the event condition information, and the learned model will be described later.

The storage 120 is achieved by, for example, a semiconductor memory including a RAM and a flash memory, a hard disk, or an optical disk. The storage 120 is also referred to as a storage.

The input interface 130 is, for example, a mouse or a keyboard. The input interface 130 receives various input operations from an operator, converts the received input operations to electric signals and outputs the electric signals to the processing circuitry 150. The input interface 130 may be, for example, electric signal processing circuitry receiving electric signals corresponding to input operations from external input equipment provided separately from the medical information processing apparatus 100, and outputting the electric signals to the processing circuitry 150. The display 140 is a liquid crystal display or a cathode-ray tube (CRT) display. The display 140 is an example of a screen in the present embodiment. In addition, the display 140 is an example of a hardware display device. The hardware display device may be a device separated from the medical information processing apparatus 100.

In the present embodiment, the operator of the medical information processing apparatus 100 is, for example, a doctor or a manager of a medical institution.

The processing circuitry 150 has an acquisition function 151, a model generation function 152, a display control function 153, a receiving function 154, and a simulation function 155. The acquisition function 151 is an example of an acquisitor. The model generation function 152 is an example of a generator. The display control function 153 is an example of a display controller. The receiving function 154 is an example of a receiver. The simulation function 155 is an example of a simulator.

The acquisition function 151 acquires various information from the electronic medical record storage apparatus 300 via the network 900 and the NW interface 110. For example, the acquisition function 151 acquires the medical record information stored in the electronic medical record storage apparatus 300 and stores the information in the storage 120.

Figure 2:
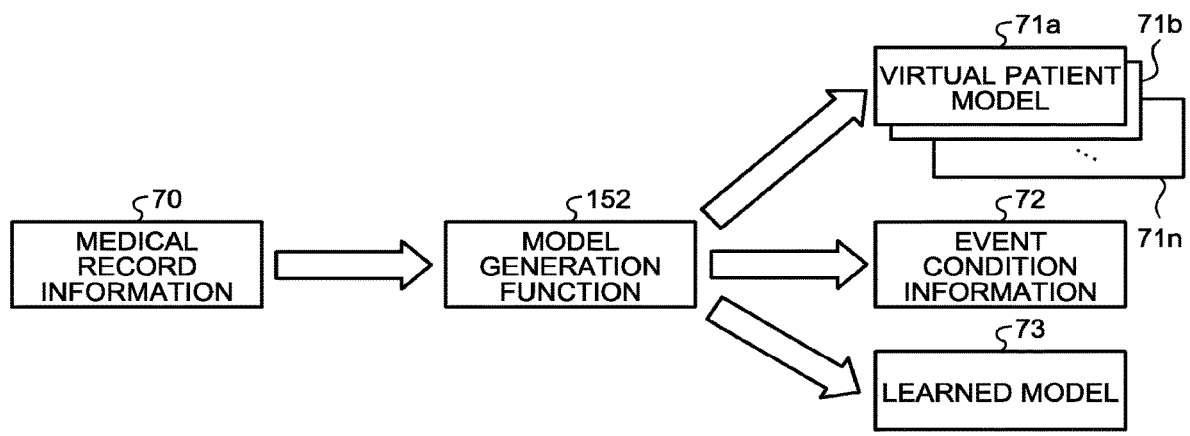
FIG. 2 is a view for explaining information generated by a model generation function according to the first embodiment.

FIG. 2 is a view for explaining information generated by the model generation function 152 according to the present embodiment. As illustrated in FIG. 2, the model generation function 152 generates a plurality of virtual patient models 71a to 71n, event condition information 72, and a learned model 73 based on medical record information 70 acquired from the electronic medical record storage apparatus 300. In the following, the virtual patient models 71a to 71n are simply referred to as virtual patient models 71 when not particularly distinguished.

The learned model 73 is obtained by learning correlations between medical actions and test results. The learned model 73 is an example of correlation information in the present embodiment.

The acquisition function 151 acquires, from the storage 120, the virtual patient models, the event condition information, and the learned model generated by the model generation function 152 described below in executing a simulation. The acquisition function 151 sends the acquired information to the display control function 153 and the simulation function 155.

Figure 3:
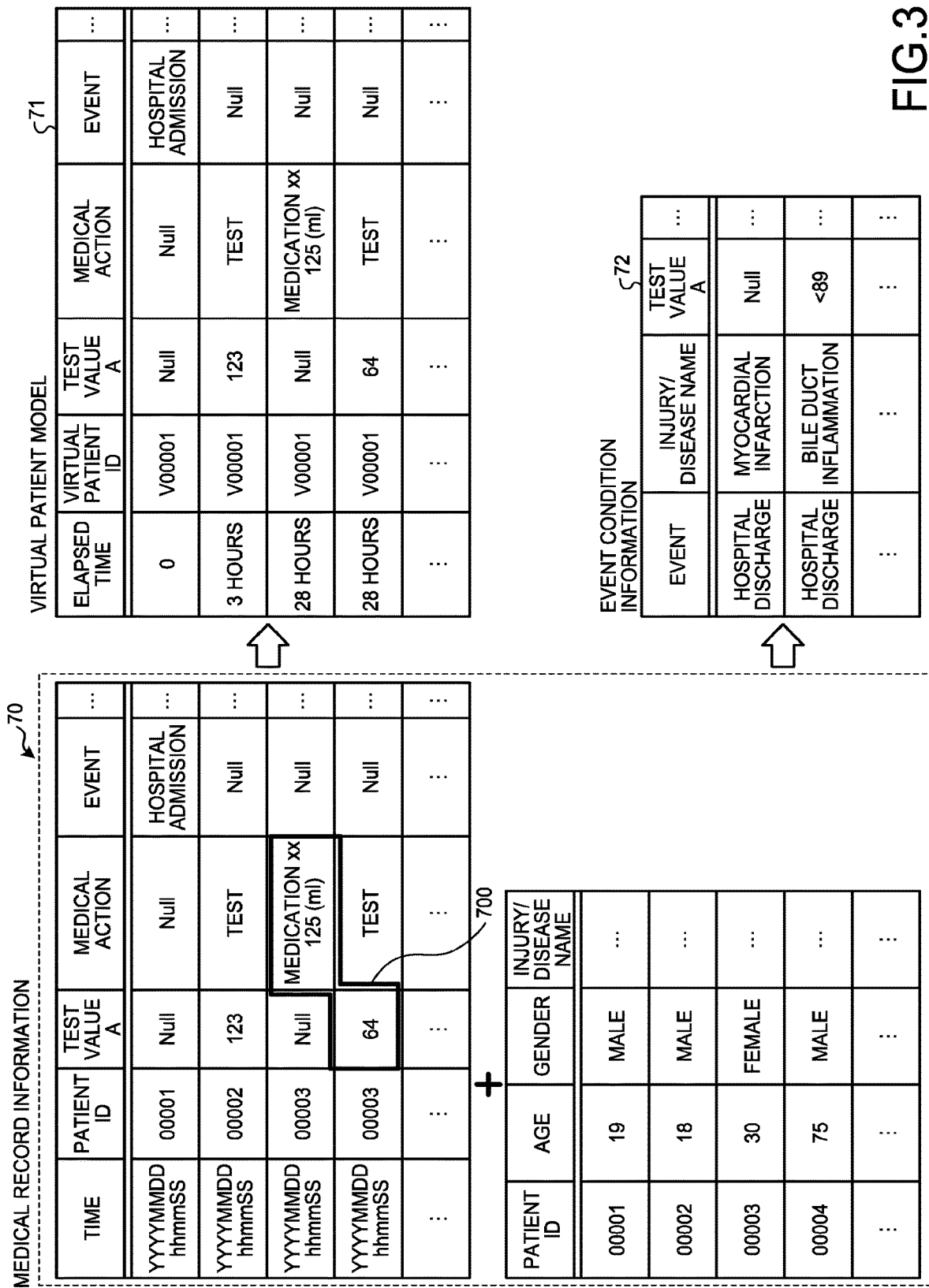
FIG. 3 is a view illustrating a detailed example of the information generated by the model generation function according to the first embodiment.

FIG. 3 is a view illustrating a detailed example of the information generated by the model generation function 152 according to the present embodiment.

The model generation function 152 classifies the medical record information 70 acquired from the electronic medical record storage apparatus 300 into a plurality of groups based on patient attribute information so as to generate the virtual patient models based on the respective classified groups. Within the medical record information 70, the model generation function 152 targets information of patients who have finished their medical treatments in the medical institution where the medical information processing apparatus 100 is installed.

In the patient attribute information, the age, gender, and injury/disease name of a patient, and the last event occurring in connection with the patient in the medical institution are associated with each other. The patient attribute information may also include other information.

The "event" in the present embodiment is a medical event occurring in connection with each of a plurality of patients in the medical institution. Examples of the event include hospital admission, hospital discharge, hospital transfer, and death. In the present embodiment, the last event occurring in connection with each of the patients in the medical institution is referred to as a "final event" of the patient. The final event is also referred to as a goal.

The model generation function 152 extracts information of a plurality of patients having common patient attribute information from a plurality of sets of the medical record information stored in the storage 120. The model generation function 152 performs statistical processing on the information of the patients having common patient attribute information, thereby generating a virtual patient model corresponding to the patient attribute information. When some sets of the patient attribute information are not completely identical, but similar to each other to some extent, the model generation function 152 may determine that the sets of patient attribute information are common.

The medical record information 70 includes records of medical treatments actually given to patients in the medical institution. In the medical record information 70, a time when an event occurs, when a test value is measured, or when a medical action is implemented, a patient ID for identifying an individual patient, a test value, a medical action, an event, and the age, gender and injury/disease name of the individual patient are associated with one another as illustrated in FIG. 3. The medical record information 70 may also include information other than the above information.

Although "test value A" is displayed as an example of the test value in FIG. 3, the medical record information 70 includes test values corresponding to various tests performed in the medical institution. In the present embodiment, examples of the test values include vital data such as a pulse, a blood pressure and a body temperature, and various test values other than the vital data. The medical record information 70 may include not only test results using numerical values, but also images captured by a computed tomography (CT) apparatus and opinions on the images as test results.

The virtual patient model 71 is information in which the patient attribute information, one or more medical actions, one or more medical events, and one or more test results are associated with one another. Each of a plurality of virtual patient models 71 is stored in the storage 120 in association with the corresponding patient attribute information regarding a virtual patient. The virtual patient model 71 is an example of virtual patient information in the present embodiment.

In the present embodiment, the virtual patient model 71 may have a database format in which the individual medical action, the implementation timing of the individual medical action, the individual event, and the occurrence timing of the individual event are associated with one another, or may have other formats in which the above sets of data are associated with one another.

The "medical action" in the present embodiment includes a medical examination and a treatment by a doctor and others. To be more specific, the medical action includes, but not limited to, tests, surgery, medication, radiotherapy, rehabilitation, and follow-up observation.

Although the "event" and the "medical action" are different in the present embodiment, the "event" may include the "medical action".

FIG. 3 shows an example in which the implementation timing of the medical action and the occurrence timing of the event are defined as elapsed times from the event "hospital admission". Other time criteria may be also used. A virtual patient ID illustrated in FIG. 3 is identification information for identifying the individual virtual patient models 71.

The virtual patient model 71 further includes time-series information indicating a change in the condition of a virtual patient. In the example illustrated in FIG. 3, the virtual patient model 71 includes information in which test values representing a change in the condition of a virtual patient, and elapsed times from the event "hospital admission" are associated with each other. The virtual patient model 71 may also include other test results.

In the present embodiment, the model generation function 152 targets, within the medical record information 70, the information of the patients who have finished their medical treatments in the medical institution where the medical information processing apparatus 100 is installed. Thus, the final event is any of the hospital discharge, the hospital transfer, or the death. The "hospital transfer" may be classified in more detail by a transfer destination.

The model generation function 152 also generates the event condition information 72 based on the medical record information 70.

The event condition information 72 defines the occurrence condition of each of the events for every combination of an event and an injury/disease name. For example, the occurrence condition of the event "hospital discharge" when the injury/disease name is "bile duct inflammation", that is, a condition under which a patient suffering from "bile duct inflammation" leaves a hospital is that the test result of the "test value A" is "less than 89". The same event has different occurrence conditions depending on the injury/disease name. The model generation function 152 may classify the occurrence condition of each of the events in more detail based on information other than the injury/disease name.

The model generation function 152 also generates the learned model 73 by learning the correlation between the medical action in each of the virtual patient models 71 and the test result in each of a plurality of virtual patients based on the medical record information 70. In other words, in the virtual patient models 71, at least one medical action is associated with at least one test result that is found to have a correlation with the at least one medical action. The model generation function 152 estimates the correlation between the at least one medical action and the at least one test result based on at least a temporal relation between a time corresponding to the at least one medical action and a time corresponding to the at least one test result. For example, when a time corresponding to a certain medical action and a time corresponding to a certain test result are within a predetermined length of time, the model generation function 152 determines that the medical action and the test result relate to each other. The time corresponding to the medical action is, for example, a time when the medical action is implemented. The time corresponding to the test result is, for example, a time when blood, etc., is collected from a subject for the test or a time when vital data is measured from a subject for the test.

For example, the implementation timing of "medication: xx 125 ml" as the "medical action" and the measurement timing of a test result "64" as the "test value A", which are enclosed by a frame 700, are assumed to be within a predetermined length of time in the example in FIG. 3. In this case, the model generation function 152 determines that the medical action of administering 125 ml of medicine xx and the test result in which the test value A is "64" relate to each other. The virtual patient model 71, the event condition information 72, and the learned model 73 may be also generated by methods other than the above methods. The model generation function 152 can employ known methods of machine learning or deep learning.

The model generation function 152 stores the virtual patient models 71, the event condition information 72 and the learned model 73 generated as described above in the storage 120.

Returning to FIG. 1, the display control function 153 displays, in the display 140, a list of the virtual patient models 71 stored in the storage 120.

FIG. 4 is a view illustrating an example of an initial display screen 50 according to the present embodiment. The display control function 153 displays the list of the virtual patient models 71 in the initial display screen 50 as illustrated in FIG. 4.

In the list of the virtual patient models 71 in the initial display screen 50, for example, identification information enabling identification of the individual virtual patient models 71 and information indicating the profiles of the individual virtual patient models 71 are displayed. In the example in FIG. 4, the display control function 153 displays, in the initial display screen 50, a virtual patient ID, an injury/disease name, condition on entering a hospital, a gender, an age, a final event, and whether an advanced medical care is applied, for each of the virtual patient models 71. The information indicating the profiles of the individual virtual patient models 71 may be any information that can be used as reference when a doctor, a hospital manager, and others select the individual virtual patient model 71.

When the receiving function 154 described later receives an operation of selecting one of the virtual patient models 71 by an operator, the display control function 153 displays a simulation screen 51 of the selected virtual patient model 71 in the display 140. In the present embodiment, the simulation screen 51 is a screen displaying the contents of the selected virtual patient model 71. To be more specific, the display control function 153 displays the event(s) and the medical action(s) included in the selected virtual patient model in time series in the display 140.

Figure 5:
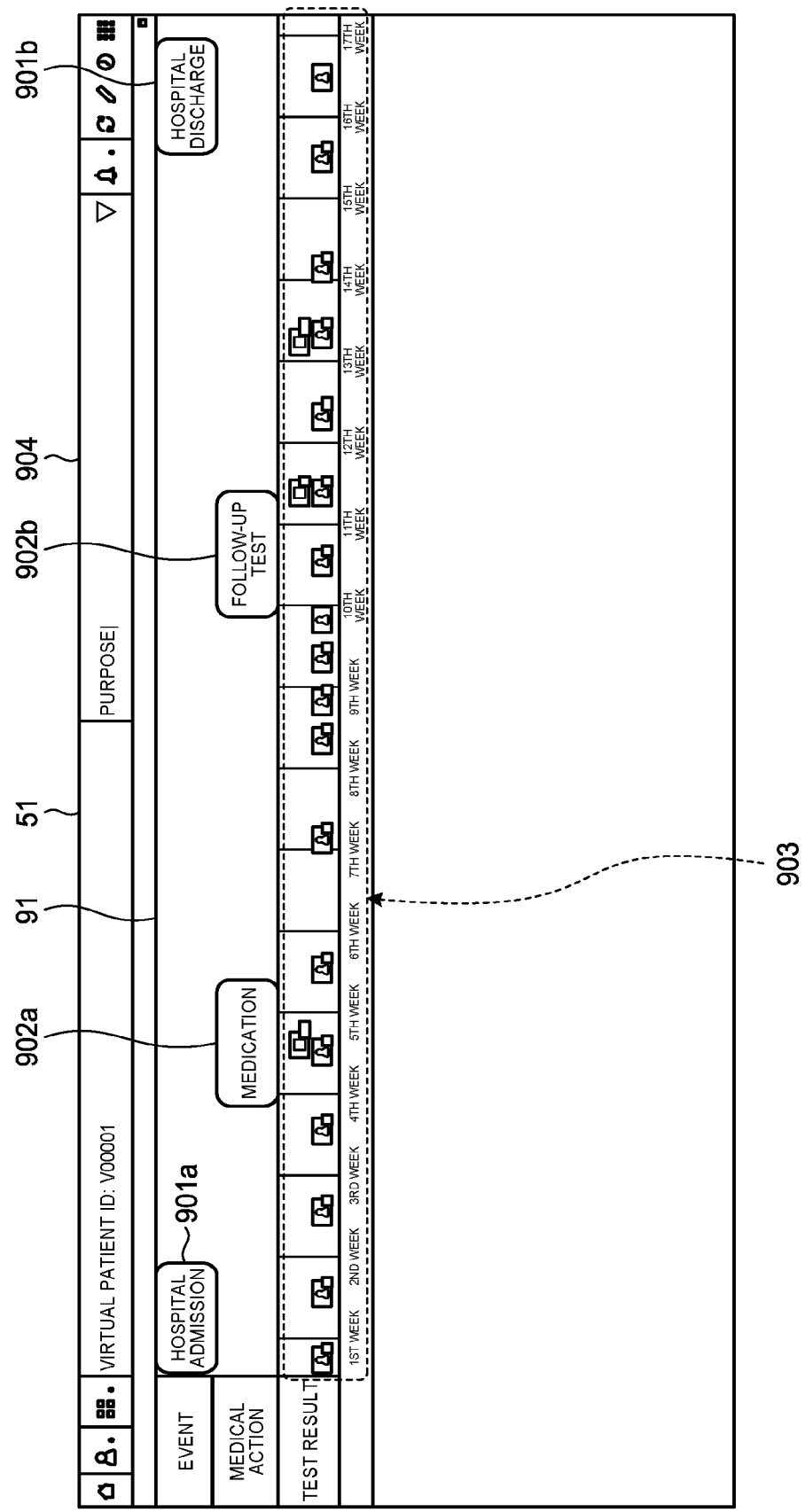
FIG. 5 is a view illustrating an initial display example of a simulation screen 51 of a virtual patient model according to the first embodiment.

FIG. 5 is a view illustrating an initial display example of the simulation screen 51 of the virtual patient model 71 according to the present embodiment. In an initial display state, no information has been changed by the operator yet. Thus, the simulation screen 51 displays the contents of the virtual patient model 71 stored in the storage 120.

In the example in FIG. 5, the display control function 153 displays events occurring in connection with a virtual patient ID "V00001", medical actions given to the virtual patient ID "V00001", and estimated test results in time series in a timeline box 91 based on the occurrence timings of the events, the implementation timings of the medical actions, and the measurement timings of the test results.

In FIG. 5, an icon 901a represents the occurrence of the event "hospital admission", and an icon 901b the occurrence of the event "hospital discharge". The final event of the virtual patient ID "V00001" is the "hospital discharge". In the following, an icon representing any event is referred to as an icon 901.

An icon 902a represents the medical action "medication", and an icon 902b the medical action "follow-up test". In the following, an icon representing any medical action is referred to as an icon 902.

A plurality of icons 903 represent links to data indicating various test results. When the receiving function 154 described later receives an operation of selecting one of the icons 903 by the operator, the display control function 153 displays a test result related to the selected icon 903 in the display 140. Examples of the data indicating various test results include vital data, electronic medical records, test result reports, and captured images.

The display control function 153 also displays a list box 904 capable of receiving selection of a simulation purpose in the simulation screen 51. The operator can select the simulation purpose by operating the list box 904, to thereby execute various simulations on the virtual patient model 71.

Examples of the simulation purpose include, but not limited to, "shorten a period from hospital admission to discharge". The display control function 153 may also display a screen offering a simulation specific to the purpose "shorten a period from hospital admission to discharge" without providing the list box 904.

The display control function 153 changes display of the event or the medical action based on the operation received by the receiving function 154, the learned model 73 and the event condition information 72.

Figure 6:
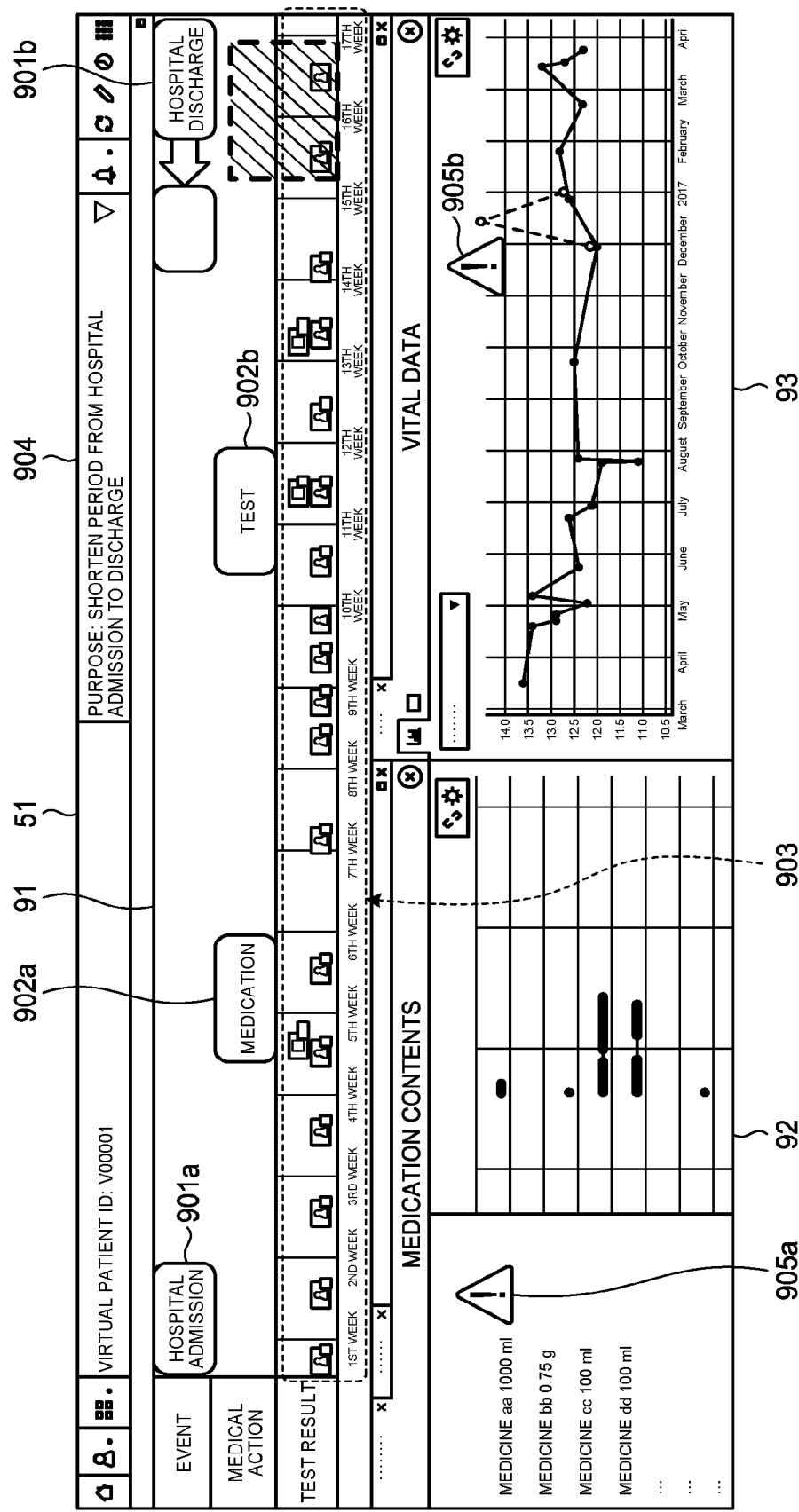
FIG. 6 is a view illustrating an example of the simulation screen after starting a simulation according to the first embodiment.

FIG. 6 is a view illustrating an example of the simulation screen 51 after starting a simulation according to the present embodiment. The simulation screen 51 illustrated in FIG. 6 shows a state after the operator selects the purpose "shorten a period from hospital admission to discharge".

In the present embodiment, when the purpose "shorten a period from hospital admission to discharge" is selected, the simulation function 155 described later identifies the occurrence timing of the event "hospital discharge" as a target to be changed. The simulation function 155 also identifies the medical action and the test result influencing the occurrence timing of the event "hospital discharge".

The display control function 153 displays the medical action and the test result influencing the occurrence timing of the target event in the simulation screen 51. In the example in FIG. 6, the medical action influencing the occurrence timing of the event "hospital discharge" is assumed to be the "medication". In this case, the display control function 153 displays the detailed contents of the medication for the virtual patient ID "V00001" in a medication content display box 92.

The medication content display box 92 is an area where the operator can perform an input operation. For example, the operator can change a medication period, a medicine dose, and a medicine type. When the simulation function 155 determines that the operation of changing the medical action by the operator conflicts with the guidelines, the display control function 153 displays a warning in the display 140. In the example in FIG. 6, the display control function 153 displays an icon 905a representing the warning in the medication content display box 92.

In the example in FIG. 6, the test result influencing the occurrence timing of the event "hospital discharge" is assumed to be the measurement result of the vital data. The display control function 153 displays a graph representing the measurement result of the vital data in a test result display box 93. Values of the measurement result of the vital data are registered as the test values in the virtual patient model 71.

When the operator changes contents of the medical action, the simulation function 155 estimates a change in the test result. The display control function 153 changes display of the test result based on the estimation result of the simulation function 155. For example, the display control function 153 displays the changed measurement result of the vital data by a dashed line in the example in FIG. 6.

When the simulation function 155 determines that the change in the test result exceeds a predetermined change amount, the display control function 153 displays a warning in the display 140. In the example in FIG. 6, the display control function 153 displays an icon 905b representing the warning in the test result display box 93.

The display control function 153 changes a display position of the event in accordance with the occurrence timing of the event estimated by the simulation function 155. In the example in FIG. 6, the display control function 153 changes the display position of the event "hospital discharge" in accordance with a change in the occurrence timing. The display control function 153 also grays out or deletes the medical action(s) and the test result(s) that become unnecessary by advancing the occurrence timing of the event "hospital discharge".

Although the event as the target whose occurrence timing is changed is the "hospital discharge" in the example in FIG. 6, the target may be another event. Simulations on the occurrence timing of the event include not only the simulation of advancing the occurrence timing but also a simulation of delaying the occurrence timing.

Returning to FIG. 1, the receiving function 154 receives various operations by the operator via the input interface 130. The receiving function 154 sends the contents of the received operations to the display control function 153 or the simulation function 155.

To be more specific, the receiving function 154 receives an operation of selecting one of the virtual patient models 71 by the operator in the initial display screen 50. The receiving function 154 receives an operation of changing the event or the medical action displayed in the simulation screen 51 by the operator. The receiving function 154 receives an operation of selecting the simulation purpose by operating the list box 904 by the operator. The receiving function 154 receives an operation of storing a simulation result by the operator. These operations are merely examples, and the receiving function 154 may receive other operations.

The simulation function 155 executes a simulation on a medical treatment plan based on the operation of the operator received by the receiving function 154, the virtual patient model 71, the learned model 73, and the event condition information 72. To be more specific, the simulation function 155 estimates a change in the test result of the virtual patient model 71 displayed in the display 140 in accordance with the operation of changing the medical action, and the learned model 73. The simulation function 155 also estimates a timing when the test result satisfies the occurrence condition of the event as the occurrence timing of the event.

FIG. 7 is a view for explaining processing of the simulation function 155 according to the present embodiment. The simulation function 155 identifies the virtual patient model 71 as a simulation target out of the virtual patient models 71 stored in the storage 120 based on the selection of the virtual patient model 71 by the operator.

The simulation function 155 also identifies the event as the target for changing the occurrence timing based on the simulation purpose selected by the operator. A correspondence relation between the purpose and the event as the target for changing the occurrence timing is defined in advance. Alternatively, the model generation function 152 may specify the correspondence relation between the purpose and the event as the target for changing the occurrence timing based on the medical record information 70.

The simulation function 155 identifies the medical action and the test result influencing the occurrence timing of the event related to the selected purpose based on the learned model 73 and the event condition information 72. To be more specific, the simulation function 155 identifies the medical action influencing the occurrence timing of the event related to the selected purpose based on the event condition information 72. The simulation function 155 also identifies the medical action influencing the identified occurrence condition based on the learned model 73.

For example, in the example described using FIG. 3, when the injury/disease name of the virtual patient is "bile duct inflammation", a condition under which the occurrence of the event "hospital discharge" is allowed is that the test result of the "test value A" is "less than 89". In this case, the simulation function 155 identifies the medical action influencing the test result of the "test value A" based on the learned model 73.

The simulation function 155 also simulates a change in the test result based on the operation of the operator and the learned model 73. For example, when the operator changes the medication contents, the simulation function 155 inputs the changed medication contents to the learned model 73, and estimates the test result based on the changed medication contents. For example, when the operator changes the dose of a certain medicine, the simulation function 155 estimates a change in the vital data of the virtual patient based on the changed dose and the learned model 73.

The simulation function 155 estimates a timing when the occurrence condition of the event as the target for changing the occurrence timing is satisfied based on the estimated test result. For example, when the event as the target for changing the occurrence timing is the "hospital discharge, the simulation function 155 estimates a timing when the test result satisfies the occurrence condition of the event "hospital discharge" as the occurrence timing of the event "hospital discharge".

The simulation function 155 sends the various identified information to the display control function 153. To be more specific, the simulation function 155 sends the identified event as the target for changing the occurrence timing, and the medical action and the test result influencing the occurrence timing of the event to the display control function 153.

The simulation function 155 also sends the simulation result of the test result, and the estimated occurrence timing of the event to the display control function 153.

When the receiving function 154 receives the operation of storing the simulation result by the operator, the simulation function 155 stores the changed virtual patient model 71 in the storage 120. The virtual patient model 71 changed in accordance with a purpose selected by a doctor and others can be used as a reference medical treatment plan in a medical institution to which the doctor belongs.

The simulation function 155 also determines whether the contents of the medical action changed by the operation conflict with the guidelines. For example, when the medicine dose inputted by the operator exceeds the upper limit defined in the guidelines stored in the storage 120, the simulation function 155 determines that the dose conflicts with the guidelines. When determining that the operation of changing the medical action by the operator conflicts with the guidelines, the simulation function 155 notifies the display control function 153.

The simulation function 155 also determines whether the change in the test result based on the operation of changing the medical action by the operator, for example, the change in the vital data exceeds a predetermined change amount. For example, the predetermined change amount is a change amount possibly giving adverse physiological effects on a patient. The predetermined change amount as a criterion for determination differs depending on the patient attribute information. When determining that the change in the test result exceeds the predetermined change amount, the simulation function 155 notifies the display control function 153.

The criterion for determination is not limited to the change amount. For example, the simulation function 155 may determine whether the change in the test result based on the operation of changing the medical action by the operator possibly gives adverse physiological effects on the patient based on whether the changed test result is included within a normal range.

For example, the acquisition function 151, the model generation function 152, the display control function 153, the receiving function 154, and the simulation function 155 as the constituent elements of the processing circuitry 150 are stored in the storage 120 as computer-executable programs. The processing circuitry 150 reads the respective computer programs out of the storage 120 and executes the respective read computer programs to achieve the functions corresponding to the respective computer programs. In other words, the processing circuitry 150 reading the respective computer programs has the respective functions illustrated in the processing circuitry 150 in FIG. 1. Although it has been described that the single processing circuitry 150 achieves the respective processing functions including the acquisition function 151, the model generation function 152, the display control function 153, the receiving function 154, and the simulation function 155 in FIG. 1, a plurality of independent processors may be combined to form the processing circuitry 150, and the respective processors may execute the respective computer programs to achieve the respective processing functions.

The term "processor" used in the above description includes, for example, central processing units (CPUs), graphics processing units (GPUs), or circuits such as application specific integrated circuits (ASICs) and programmable logic devices including simple programmable logic devices (SPLDs), complex programmable logic devices (CPLDs), and field programmable gate arrays (FPGAs). The computer programs may be directly incorporated into the circuitry of the processor instead of storing the computer programs in the storage 120. In this case, the processor reads and executes the computer programs incorporated into the circuitry so as to achieve the functions.

The computer programs executed by the processor may be stored in a computer-readable storage medium such as a compact disc read-only memory (CD-ROM), a flexible disk (FD), a compact disc-recordable (CD-R), and a digital versatile disc (DVD). The computer programs may be stored in a computer connected to a network such as the Internet, and downloaded via the network so as to be provided or distributed.

Next, a flow of processing executed in the medical information processing apparatus 100 according to the present embodiment will be described.

Figure 8A:
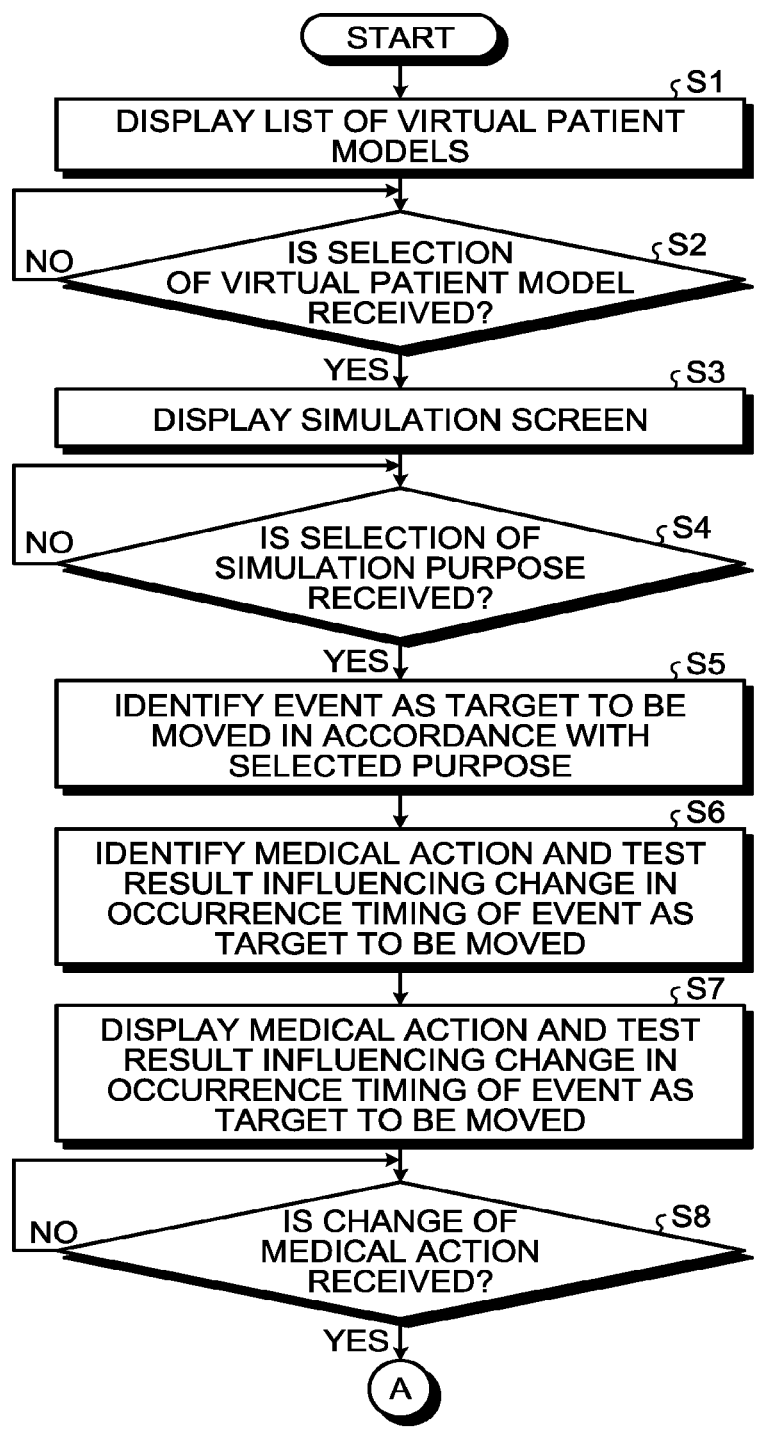
FIG. 8A is a flowchart illustrating an example of a flow of simulation processing for the virtual patient model according to the first embodiment.
Figure 8B:
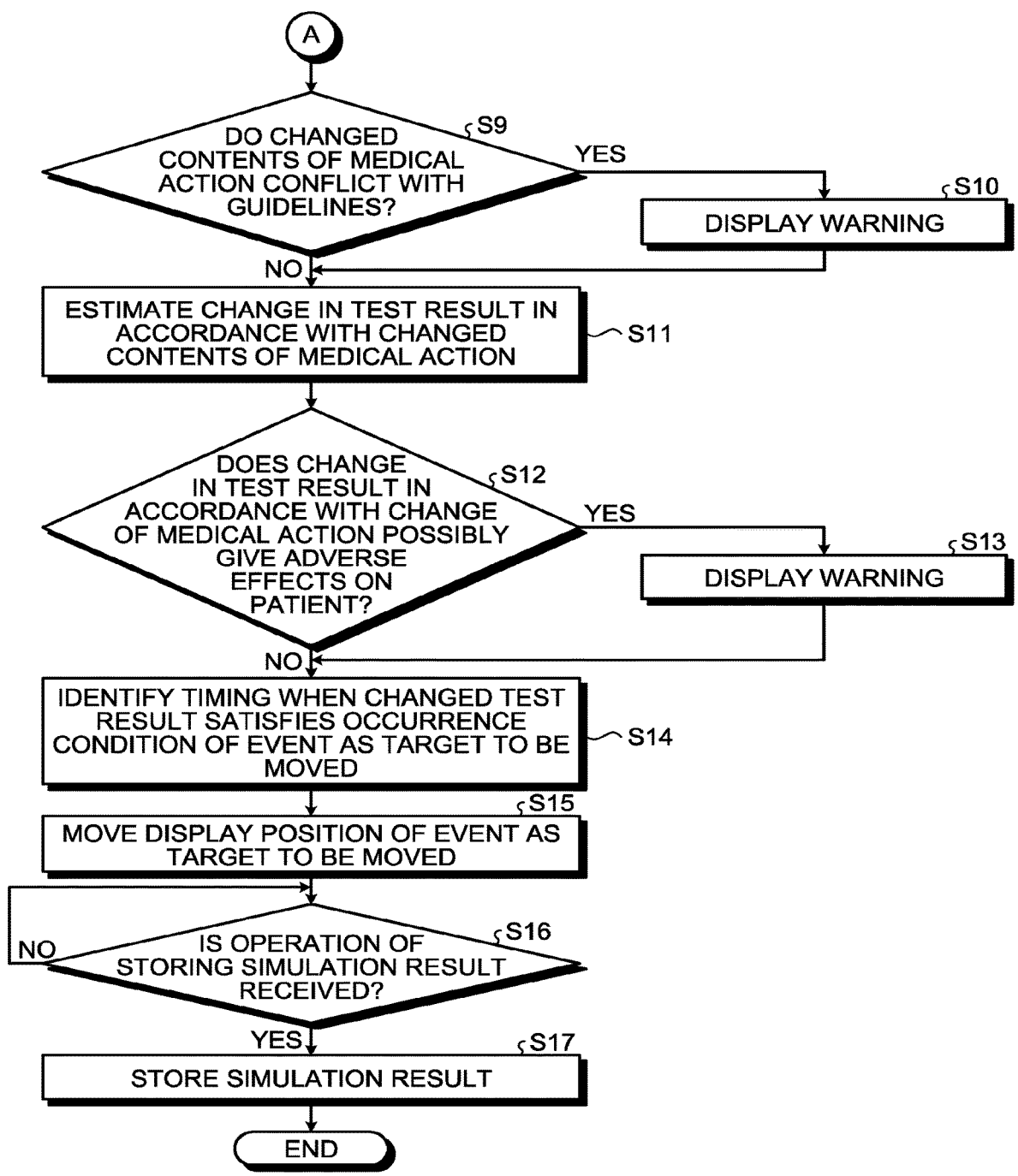
FIG. 8B is a continuation of the flowchart illustrated in FIG. 8A.

FIGS. 8A and 8B are a flowchart illustrating an example of a flow of simulation processing for the virtual patient model 71 according to the present embodiment. The model generation function 152 generates the virtual patient models 71, the event condition information 72, and the learned model 73 based on the medical record information 70 acquired from the electronic medical record storage apparatus 300 and stores the information in the storage 120 before the start of the processing in the flowchart.

When the processing starts, the acquisition function 151 acquires the virtual patient models 71 from the storage 120 and sends the virtual patient models 71 to the display control function 153. The display control function 153 displays the list of the virtual patient models 71 in the display 140 as the initial display screen 50 (S1).

The receiving function 154 determines whether the selection of one of the virtual patient models 71 is received in the initial display screen 50 (S2). When determining that the selection of the virtual patient model 71 has not been received ("No" at S2), the receiving function 154 repeats the step S2.

When determining that the selection of the virtual patient model 71 has been received ("Yes" at S2), the receiving function 154 sends the information for identifying the selected virtual patient model 71 to the display control function 153. In this case, the display control function 153 displays the simulation screen 51 of the selected virtual patient model 71 in the display 140 in the initial display state (S3). The acquisition function 151 acquires the selected virtual patient model 71, the event condition information 72, and the learned model 73 from the storage 120, and sends the information to the simulation function 155.

The receiving function 154 determines whether the selection of the simulation purpose is received (S4). When determining that the selection of the simulation purpose has not been received ("No" at S4), the receiving function 154 repeats the step S4.

When determining that the selection of the simulation purpose has been received ("Yes" at S4), the receiving function 154 sends the information for identifying the selected purpose to the simulation function 155. In this case, the simulation function 155 identifies the event as a target to be moved in accordance with the selected purpose (S5).

Subsequently, the simulation function 155 identifies the medical action and the test result influencing the change in the occurrence timing of the event as the target to be moved (S6). To be more specific, the simulation function 155 identifies the occurrence condition of the event as the target for changing the occurrence timing based on the event condition information 72 stored in the storage 120. The simulation function 155 also identifies the medical action influencing the identified occurrence condition based on the learned model 73. The simulation function 155 then sends the medical action and the test result influencing the change in the occurrence timing of the event as the target to be moved to the display control function 153.

The display control function 153 displays the medical action and the test result influencing the change in the occurrence timing of the event as the target to be moved in the simulation screen 51 (S7).

In the example in FIG. 6, the medical action influencing the occurrence timing of the event "hospital discharge" is the "medication". Thus, the display control function 153 displays the medication content display box 92 displaying the medication contents in the simulation screen 51. The display control function 153 also displays the test result display box 93 displaying the test result of the vital data influencing the occurrence timing of the event "hospital discharge" in the simulation screen 51. When there are a plurality of medical actions or test results influencing the change in the occurrence timing of the event as the target to be moved, the display control function 153 may provide a plurality of display boxes in the simulation screen 51. When the simulation function 155 identifies a particular medicine influencing the change in the occurrence timing of the event as the target to be moved out of medicines administered to the virtual patient, the display control function 153 may emphasize and display the medicine in the medication content display box 92.

Subsequently, the receiving function 154 determines whether the change of the medical action is received (S8). When determining that the change of the medical action has not been received ("No" at S8), the receiving function 154 repeats the step S8.

When determining that the change of the medical action has been received ("Yes" at S8), the receiving function 154 sends the changed contents of the medical action to the simulation function 155. In this case, the simulation function 155 determines whether the changed contents of the medical action conflict with the guidelines (S9).

When determining that the changed contents of the medical action conflict with the guidelines ("Yes" at S9), the simulation function 155 notifies the display control function 153. In this case, the display control function 153 displays the warning in the simulation screen 51 (S10). In the example in FIG. 6, the display control function 153 displays the icon 905a representing the warning in the medication content display box 92 of the simulation screen 51.

When determining that the changed contents of the medical action do not conflict with the guidelines ("No" at S9), the simulation function 155 proceeds to step S11. The simulation function 155 estimates the change in the test result in accordance with the changed contents of the medical action and the learned model 73 (S11).

The flowchart shows an example in which the simulation function 155 executes the step S11 even when determining that the changed contents of the medical action conflict with the guidelines. The simulation function 155 does not have to receive the change when determining that the changed contents of the medical action conflict with the guidelines.

The simulation function 155 determines whether the change in the test result in accordance with the change of the medical action possibly gives adverse effects on the patient based on the estimated change in the test result (S12). For example, when the change amount of the test result exceeds the predetermined change amount, the simulation function 155 determines that the change in the test result in accordance with the change of the medical action possibly gives adverse effects on the patient.

When determining that the change in the test result in accordance with the change of the medical action possibly gives adverse effects on the patient ("Yes" at S12), the simulation function 155 notifies the display control function 153. In this case, the display control function 153 displays the warning in the simulation screen 51 (S13). In the example in FIG. 6, the display control function 153 displays the icon 905*b* representing the warning in the test result display box 93 of the simulation screen 51.

When determining that the change in the test result in accordance with the change of the medical action does not possibly give adverse effects on the patient ("No" at S12), the simulation function 155 proceeds to step S14. The simulation function 155 then identifies the timing when the changed test result satisfies the occurrence condition of the event as the target to be moved (S14). In the example in FIG. 6, the test result of the vital data satisfies the occurrence condition of the event "hospital discharge" on the 15th week after the hospital admission by the change in the vital data in accordance with the change of the medication contents. In this case, the simulation function 155 estimates the 15th week after the hospital admission as the changed occurrence timing of the event. The simulation function 155 sends the estimated occurrence timing of the event to the display control function 153.

The flowchart shows an example in which the simulation function 155 executes the step S14 even when determining that the change in the test result in accordance with the change of the medical action possibly gives adverse effects on the patient. The simulation function 155 does not have to receive the change when determining that the change in the test result in accordance with the change of the medical action possibly gives adverse effects on the patient.

The simulation function 155 moves the display position of the event as the target to be moved (S15). In the example in FIG. 6, the icon 901*b* representing the "hospital discharge" located at a display position corresponding to the 17th week after the hospital admission in the initial display state is moved to a display position corresponding to the 15th week after the hospital admission.

The receiving function 154 determines whether the operation of storing the simulation result is received (S16). When determining that the operation of storing the simulation result has not been received ("No" at S16), the receiving function 154 repeats the step S16. When determining that the operation of storing the simulation result has been received ("Yes" at S16), the receiving function 154 notifies the simulation function 155 that the operation has been received.

The simulation function 155 stores the simulation result in the storage 120 as the changed virtual patient model 71 when the receiving function 154 receives the operation of storing the simulation result by the operator (S17). The simulation function 155 stores the simulation result, thereby defining a new medical treatment model in the medical institution.

As described above, the medical information processing apparatus 100 according to the present embodiment displays the event(s) and the medical action(s) associated with the virtual patient model 71 selected from the virtual patient models 71 in time series in the display 140 based on the occurrence timing(s) of the event(s) and the implementation timing(s) of the medical action(s). By displaying the event(s) and the medical action(s) associated with the virtual patient model 71 in time series, the medical information processing apparatus 100 according to the present embodiment enables to easily grasp a medical treatment process that a patient corresponding to the patient attribute information of the displayed virtual patient model 71 undergoes until reaching the final event. Thus, the medical information processing apparatus 100 according to the present embodiment assists a doctor and others to examine or improve the process that the patient undergoes until reaching the final event.

The medical information processing apparatus 100 according to the present embodiment also changes the display of the event or the medical action based on the operation of changing the event or the medical action, the learned model 73, and the event condition information 72. Thus, the medical information processing apparatus 100 according to the present embodiment enables a doctor and others to easily simulate the occurrence timing of the event by changing the medical action.

For example, a manager of a medical institution can use the medical information processing apparatus 100 according to the present embodiment in simulating the occurrence timing of the final event "hospital discharge" in order to improve the turnover rate of hospital beds. The medical information processing apparatus 100 according to the present embodiment enables the manager of the medical institution to easily examine an effective medical action for advancing the occurrence timing of the final event "hospital discharge" by changing the medical action and simulating the occurrence timing of the final event "hospital discharge". The medical information processing apparatus 100 according to the present embodiment can visualize the result estimated by changing the medical action, thereby assisting an efficient discussion by a plurality of doctors in a scene such as a conference for discussing a medical treatment policy.

For example, when a doctor and others specify the target occurrence timing of the event, a computer may estimate, based on the target occurrence timing, a medical action that cannot be implemented by the doctor who has executed the simulation. In contrast, the medical information processing apparatus 100 according to the present embodiment simulates the occurrence timing of the event in accordance with the result obtained by receiving the operation by a doctor and others, thereby achieving the simulation based on the medical action that can be actually implemented by the doctor.

The medical information processing apparatus 100 according to the present embodiment estimates the change in the test result of the virtual patient model 71 displayed in the display 140 in accordance with the operation of changing the medical action, and the learned model 73. The medical information processing apparatus 100 according to the present embodiment also estimates the timing when the test result satisfies the occurrence condition of the event as the occurrence timing of the event. For example, the medical information processing apparatus 100 according to the present embodiment estimates a timing when the test result of the virtual patient allows the virtual patient to leave a hospital as the occurrence timing of the event "hospital discharge". Thus, the medical information processing apparatus 100 according to the present embodiment can reduce a problem of proposing an impossible medical treatment plan in the medical institution, for example, proposing to allow a patient who cannot leave a hospital yet to leave the hospital.

When determining that the contents of the medical action changed by the operation conflict with the guidelines, the medical information processing apparatus 100 according to the present embodiment displays the warning in the display 140. Thus, the medical information processing apparatus 100 according to the present embodiment can notify the operator that the operation of changing the medical action does not satisfy medical or ethical conditions. Consequently, the medical information processing apparatus 100 according to the present embodiment can reduce a problem in which a doctor and others create a medical treatment plan not satisfying medical or ethical conditions.

When determining that the change in the test result by the operation of changing the medical action exceeds the predetermined change amount, the medical information processing apparatus 100 according to the present embodiment displays the warning in the display 140. Thus, the medical information processing apparatus 100 according to the present embodiment can reduce a problem in which a doctor and others create a medical treatment plan possibly giving adverse effects on the patient condition.

The medical information processing apparatus 100 according to the present embodiment identifies the medical action and the test result influencing the occurrence timing of the event related to the selected simulation purpose based on the learned model 73 and the event condition information 72, and displays the identified medical action and test result in the display 140. Thus, the medical information processing apparatus 100 according to the present embodiment enables a doctor and others to easily grasp the medical action to be changed in accordance with the purpose, thereby achieving the efficient simulation.

The medical information processing apparatus 100 according to the present embodiment also generates the virtual patient model 71 based on the medical record information having the common patient age, gender, and injury/disease name, and the common final event out of the sets of medical record information indicating the records of medical actions actually given to a plurality of patients in the medical institution. Thus, the medical information processing apparatus 100 according to the present embodiment can visualize, as the virtual patient model 71, a past typical medical treatment process of each of the sets of patient attribute information in the medical institution.

The medical information processing apparatus 100 generates the event condition information 72 and the learned model 73 in the present embodiment. The event condition information 72 and the learned model 73 may be also generated in an external apparatus. In this case, the medical information processing apparatus 100 does not have to have the model generation function 152. The acquisition function 151 may acquire the event condition information 72 and the learned model 73 from the external apparatus.

The simulation function 155 may estimate the change in the occurrence timing of the event by the change of the medical action by using various artificial intelligence (AI) techniques other than the example described in the present embodiment. Various models used in the AIs may be generated by the medical information processing apparatus 100 or acquired from an external apparatus. In the present embodiment, the simulation function 155 estimates the change in the occurrence timing of the event by the change of the medical action. This function may be also achieved by the display control function 153. For example, the display control function 153 may estimate the change in the occurrence timing of the event by the change of the medical action by using the learned model 73 or various AIs, and change the display position of the event in accordance with the estimated occurrence timing of the event.

The learned model 73 in the present embodiment may be a "self-learning model" that acquires feedback of users to further update its internal algorithm. Although the learned model 73 stored in the storage 120 is read by the acquisition function 151 or the simulation function 155 in the present embodiment, the learned model 73 may be also incorporated into the processing circuitry 150.

The processing executed by the acquisition function 151 in the present embodiment may be executed by any of the model generation function 152, the display control function 153, or the simulation function 155.

The virtual patient model 71, which is based on the past medical record information in the medical institution where the simulation is executed in the present embodiment, may be also based on, for example, medical record information in other medical institutions or results of clinical trials.

In the present embodiment, the virtual patient model 71 and the learned model 73 have been described as separate elements. The virtual patient model 71 may include the learned model 73. In the present embodiment, the medical information processing apparatus 100 displays the simulation screen 51 and other screens in the display 140. The medical information processing apparatus 100 may display the simulation screen 51 and other screens in a display of another information processing apparatus connected to the medical information processing apparatus 100 via a network. Another information processing apparatus may be, for example, a personal computer (PC) or a mobile terminal. In this case, the display of another information processing apparatus is an example of the screen.

In the present embodiment, the display control function 153 does not display the medication content display box 92 and the test result display box 93 in the initial display state of the simulation screen 51. The display control function 153 may display the medication content display box 92 and the test result display box 93 in the initial display state.

The display of the simulation screen 51 is merely one example and is not limited thereto. For example, for an expensive medical action not covered by insurance, such as an advanced medical care, the display control function 153 may display that the medical action is not covered by insurance in the timeline box 91 or the medication content display box 92. Whether the expensive medical action not covered by insurance is applied may change the occurrence timing of the event "hospital discharge" or the like. Some patients desire such expensive medical action and other patients do not. The display control function 153 makes it easier to create a plurality of medical treatment plans targeting patients with different budgets by displaying whether the medical action is covered by insurance in the timeline box 91 or the medication content display box 92.

Second Embodiment

In the above first embodiment, the medical information processing apparatus 100 executes the simulation of changing the occurrence timing of the event. In a second embodiment, the medical information processing apparatus 100 further executes a simulation of adding a new event to the virtual patient model 71 or a simulation of substituting another event for the existing event.

The medical information processing system S and the medical information processing apparatus 100 according to the present embodiment have the same configuration as the first embodiment.

The processing circuitry 150 of the medical information processing apparatus 100 according to the present embodiment includes the acquisition function 151, the model generation function 152, the display control function 153, the receiving function 154, and the simulation function 155 similarly to the first embodiment. The acquisition function 151 and the model generation function 152 according to the present embodiment have the same functions as those of the first embodiment.

The receiving function 154 according to the present embodiment receives an operation of adding a new event to the timeline box 91 of the virtual patient model 71 selected by the operator and displayed in the display 140 in addition to having the same functions as those of the first embodiment. The receiving function 154 notifies the display control function 153 and the simulation function 155 of the event added by the operator.

In the present embodiment, the receiving function 154 also receives an operation of selecting, as the simulation purpose, to change the final event included in the virtual patient model 71. When receiving the purpose, the receiving function 154 notifies the simulation function 155.

The display control function 153 according to the present embodiment displays one or more addable event candidates in the display 140 in accordance with the selected purpose in addition to having the same functions as those of the first embodiment. The one or more addable events may be an event to be substituted for any of the already displayed events, or may be an event to be newly added. For example, the display control function 153 displays one or more other events substitutable for the final event in the display 140 as a substitutable event candidate(s) when the receiving function 154 receives the operation of selecting to change the final event as the purpose. For example, when the operator right-clicks, the display control function 153 may display the name(s) of the one or more addable or substitutable events.

Displaying the one or more addable or substitutable event candidates offers a suggestion for the operator, not an automatic event adding function. The operator may also manually input an event other than the event(s) displayed as the candidate(s) by the display control function 153.

When the operator operates to add the event(s), the display control function 153 displays the added event(s) in the display 140. In this case, the display control function 153 determines the display position(s) of the icon(s) 901 representing the event(s) in the timeline box 91 based on the occurrence timing(s) estimated by the simulation function 155.

The simulation function 155 according to the present embodiment identifies one or more events newly addable to the virtual patient model 71 in accordance with the selected purpose in addition to having the same functions as those of the first embodiment. The simulation function 155 also identifies one or more events substitutable for the event displayed in the timeline box 91 in accordance with the selected purpose.

The simulation function 155 may also identify one or more events deletable from the virtual patient model 71 in accordance with the selected purpose. A correspondence relation between the purpose and the addable, substitutable, or deletable event is defined in advance. For example, the model generation function 152 may specify the correspondence relation between the purpose and the addable or deletable event based on the medical record information 70, and store the specification result in the storage 120.

The simulation function 155 also estimates a timing when the test result included in the virtual patient model 71 selected by the operator satisfies the occurrence condition of the added or substituted event as the occurrence timing of the added or substituted event.

The simulation function 155 sends the addable or substitutable event(s) to the display control function 153. The simulation function 155 also sends the estimation result of the occurrence timing of the added or substituted event to the display control function 153.

Figure 9:
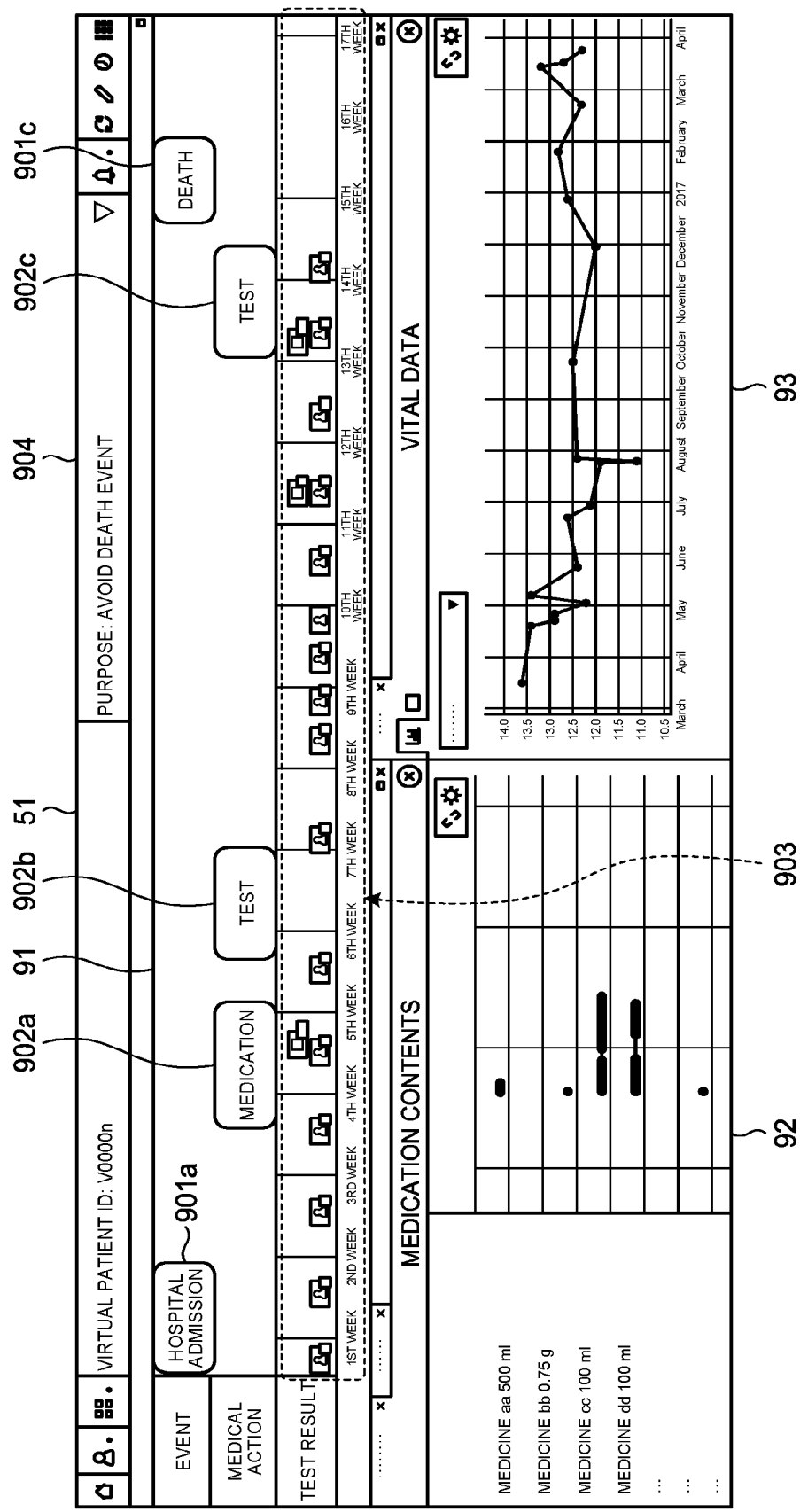
FIG. 9 is a view illustrating an example of a simulation screen according to a second embodiment.

FIG. 9 is a view illustrating an example of the simulation screen 51 according to the present embodiment. In the example in FIG. 9, a purpose "avoid a death event" is selected as the simulation purpose. In the example in FIG. 9, the final event of the virtual patient model 71 displayed in the simulation screen 51 is "death". In this case, the operation of selecting the purpose "avoid a death event" by the operator is the operation of selecting to change the final event associated with the virtual patient model 71 as the purpose.

In the example in FIG. 9, the simulation function 155 estimates the event(s) substitutable for the event "death". For example, the simulation function 155 estimates that an event "transfer to a hospice" is substitutable for the event "death". The substitutable event differs depending on the virtual patient model 71. When the patient is likely to recover, the event "hospital discharge" is substitutable for the event "death".

The simulation function 155 also identifies whether there is another event as a prerequisite for the addable or substitutable event. Events as prerequisites for the respective events are, for example, registered in the event condition information 72. Alternatively, the events as prerequisites for the respective events may be defined by the guidelines. In one example, the event as a prerequisite for "transfer to a hospice" is "explanation to a patient". This is because the patient or his/her family needs to consent to be transferred to a hospice.

Figure 10:
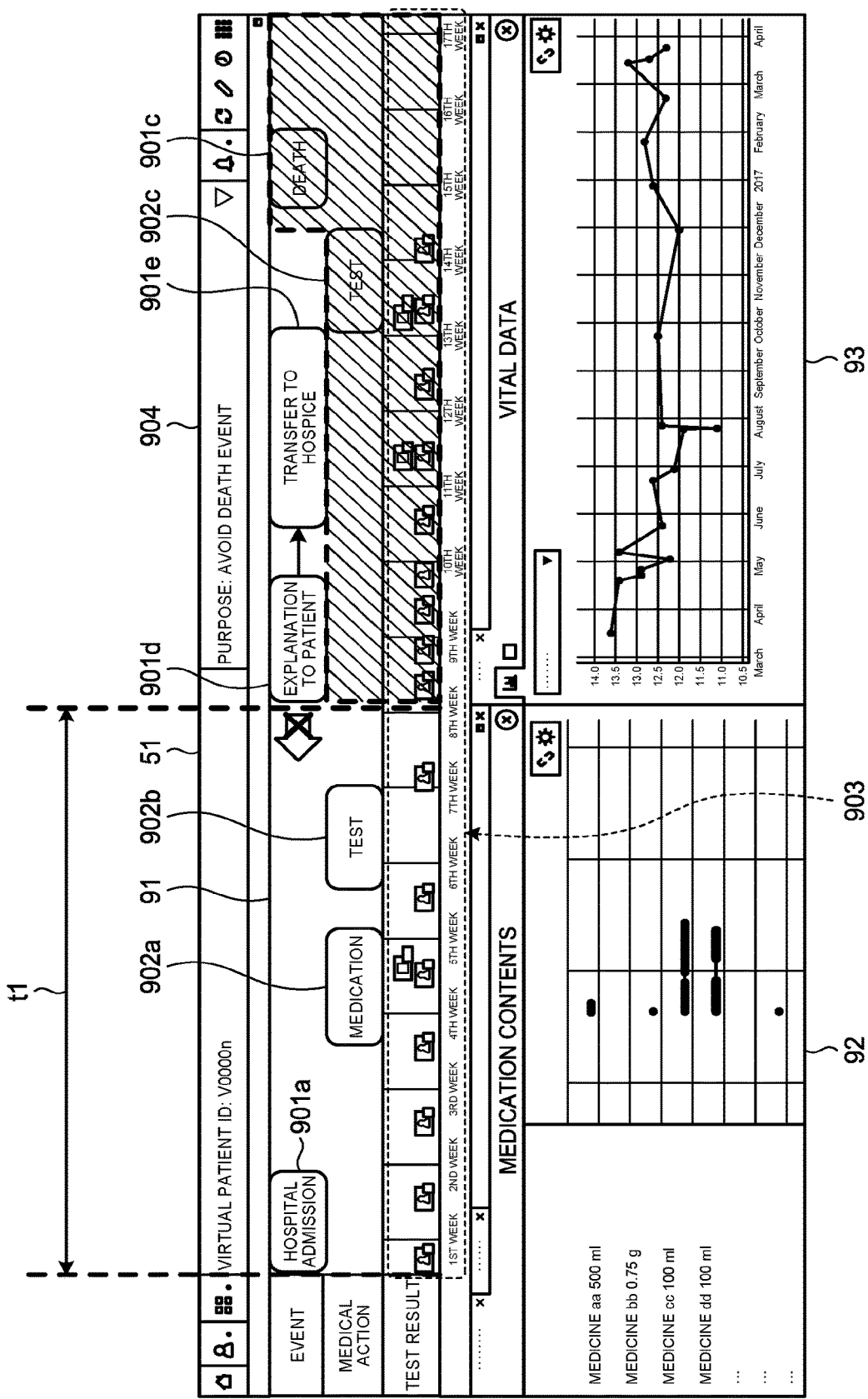
FIG. 10 is a view illustrating an example of the simulation screen after adding events according to the second embodiment.

FIG. 10 is a view illustrating an example of the simulation screen 51 after adding events according to the present embodiment. Although the display control function 153 displays the event "death" in FIG. 10, the display control function 153 may add "explanation to a patient" and "transfer to a hospice" after deleting the event "death". The medical action scheduled after the "explanation to a patient" becomes unnecessary. Thus, the display control function 153 grays out or deletes an icon 902c representing the medical action after the "explanation to a patient", and the icons 903 representing the test results after the "explanation to a patient".

In the example in FIG. 10, the occurrence condition of the event "explanation to a patient" includes that a predetermined period of time t1 has elapsed from the hospital admission, and that the "medication" represented by the icon 902a and the "test" represented by the icon 902b have already been implemented. In this case, the display control function 153 displays an icon 901d representing the event "explanation to a patient" at a display position after the elapse of the predetermined period t1 in the timeline box 91. The display control function 153 also displays an icon 901e representing the event "transfer to a hospice" at a timing after the event "explanation to a patient".

Next, a flow of processing executed in the medical information processing apparatus 100 according to the present embodiment will be described.

Figure 11A:
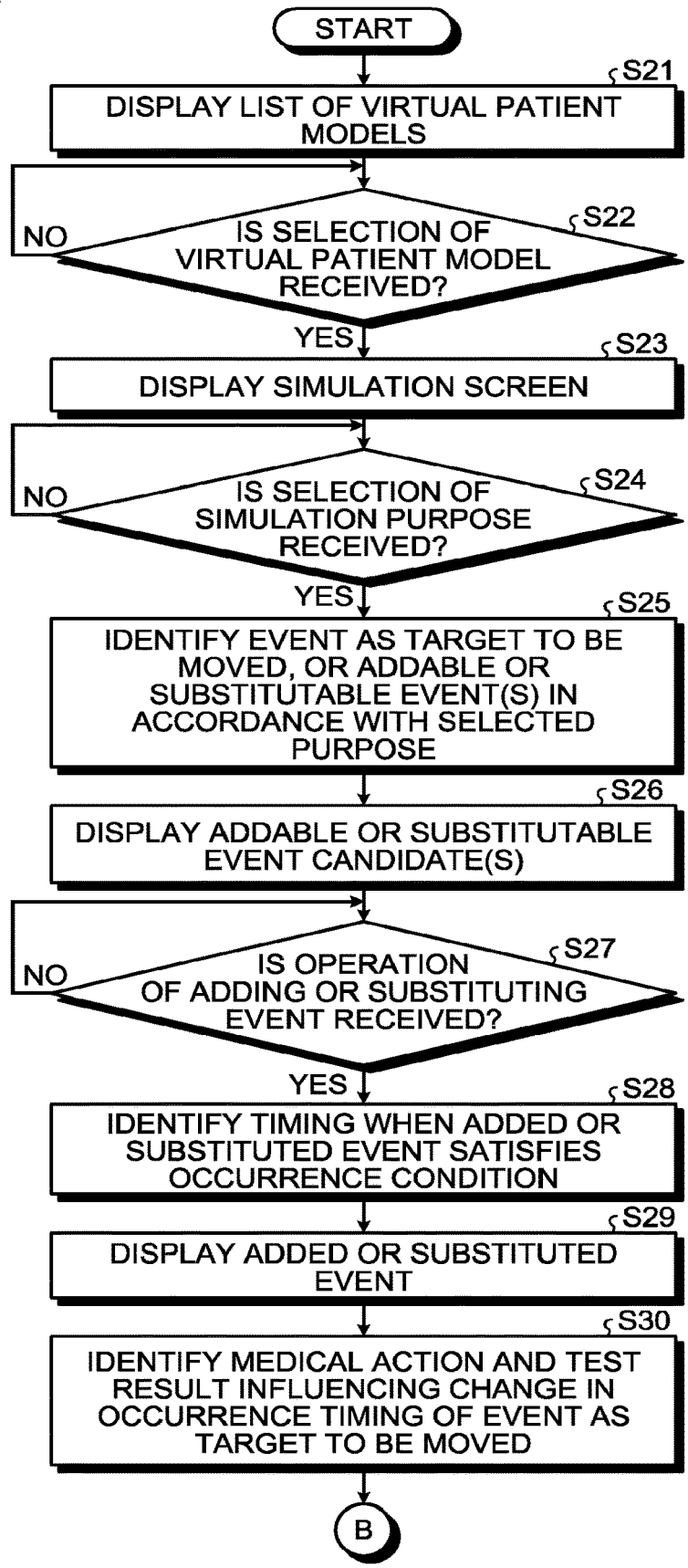
FIG. 11A is a flowchart illustrating an example of a flow of simulation processing for the virtual patient model according to the second embodiment.
Figure 11B:
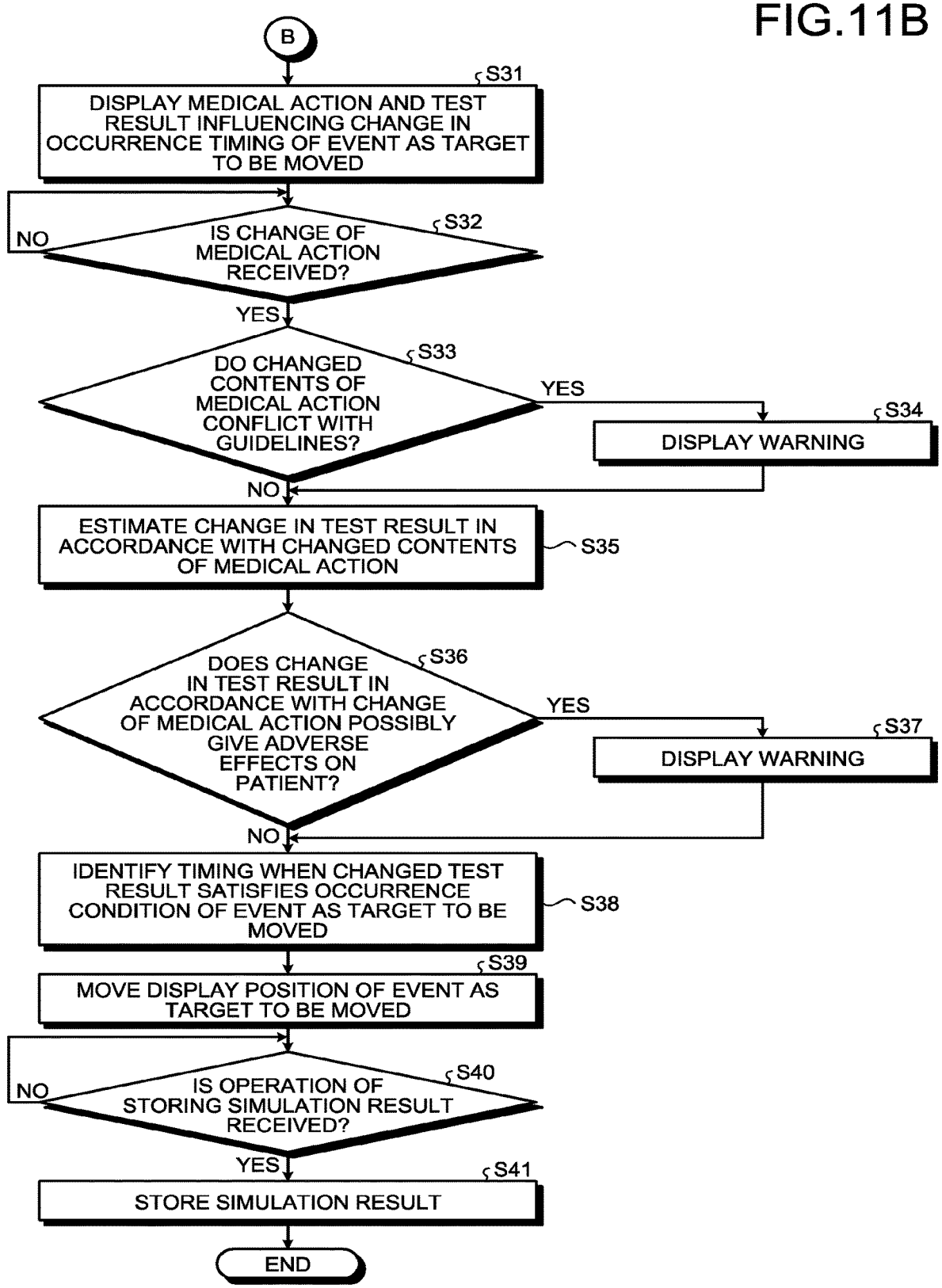
FIG. 11B is a continuation of the flowchart illustrated in FIG. 11A.

FIGS. 11A and 11B are a flowchart illustrating an example of a flow of simulation processing for the virtual patient model 71 according to the present embodiment. The step of displaying the list of the virtual patient models 71 at S21 to the step of determining whether the selection of the simulation purpose is received at S24 are similar to those from S1 to S4 in the first embodiment.

The simulation function 155 according to the present embodiment identifies the event as the target to be moved or identifies the addable or substitutable event(s) in accordance with the selected purpose (S25).

The display control function 153 displays the addable or substitutable event candidate(s) in the simulation screen 51 (S26). For example, when the receiving function 154 receives that the operator right-clicks on the timeline box 91, the display control function 153 may display the addable or substitutable event candidate(s).

The receiving function 154 then determines whether the operation of adding or substituting the event is received (S27). When determining that the operation of adding or substituting the event has not been received ("No" at S27), the receiving function 154 repeats the step S27.

When the receiving function 154 determines that the operation of adding or substituting the event has been received ("Yes" at S27), the simulation function 155 identifies the timing when the added or substituted event satisfies the occurrence condition as the occurrence timing (S28).

The display control function 153 displays the added or substituted event at a display position based on the identified occurrence timing in the timeline box 91 (S29). The step of identifying the medical action and the test result influencing the change in the occurrence timing of the event as the target to be moved at S30 to the step of storing the simulation result at S41 are similar to those from S6 to S17 in the first embodiment. When the simulation purpose is not the movement of the occurrence timing of the event, the steps regarding the movement of the occurrence timing of the event do not have to be executed.

As described above, when the new event is added, the medical information processing apparatus 100 according to the present embodiment estimates the timing when the test result included in the virtual patient model 71 selected by the operator satisfies the occurrence condition of the added event as the occurrence timing, and displays the added event at the display position based on the estimated occurrence timing. Thus, the medical information processing apparatus 100 according to the present embodiment enables a doctor and others to create a medical treatment plan for implementing an event that the doctor wants to add at an appropriate timing in addition to the advantageous effects of the first embodiment.

When receiving the operation of selecting to change the final event associated with the virtual patient model 71 displayed in the display 140 as the simulation purpose, the medical information processing apparatus 100 according to the present embodiment identifies one or more other events substitutable for the final event, and displays the event(s) as the substitutable event candidate(s). Thus, the medical information processing apparatus 100 according to the present embodiment can assist a doctor and others to consider a medical treatment plan for changing the final event of the virtual patient model 71 based on the past medical treatment records.

For example, a manager and others of a medical institution may want to reduce a death rate in the medical institution. In such a case, the medical information processing apparatus 100 presents another event(s) substitutable for the final event "death", thereby achieving a decrease in the death rate in the medical institution.

Third Embodiment

The medical information processing apparatus 100 displays the event(s), the medical action(s), and the test result(s) in the simulation screen 51 in the above first and second embodiments. In a third embodiment, a financial index during a medical treatment period is further displayed.

The medical information processing system S and the medical information processing apparatus 100 according to the present embodiment have the same configuration as the first embodiment.

The processing circuitry 150 of the medical information processing apparatus 100 according to the present embodiment includes the acquisition function 151, the model generation function 152, the display control function 153, the receiving function 154, and the simulation function 155 similarly to the first embodiment. The acquisition function 151 and the model generation function 152 according to the present embodiment have the same functions as those of the first embodiment. The receiving function 154 according to the present embodiment has the same functions as those of the second embodiment.

The display control function 153 according to the present embodiment displays, in the display 140, a financial index corresponding to the virtual patient model 71 displayed in the display 140 in addition to having the same functions as those of the first embodiment. Examples of the financial index include, but not limited to, a profit rate, costs, and sales.

The simulation function 155 according to the present embodiment calculates the financial index corresponding to the virtual patient model 71 in addition to having the same functions as those of the first embodiment. For example, the storage 120 stores accounting information such as a medical treatment fee for the individual medical action and personnel expenses. The simulation function 155 calculates a value of the financial index from when the virtual patient is hospitalized until when the virtual patient reaches the final event based on the accounting information.

Figure 12:
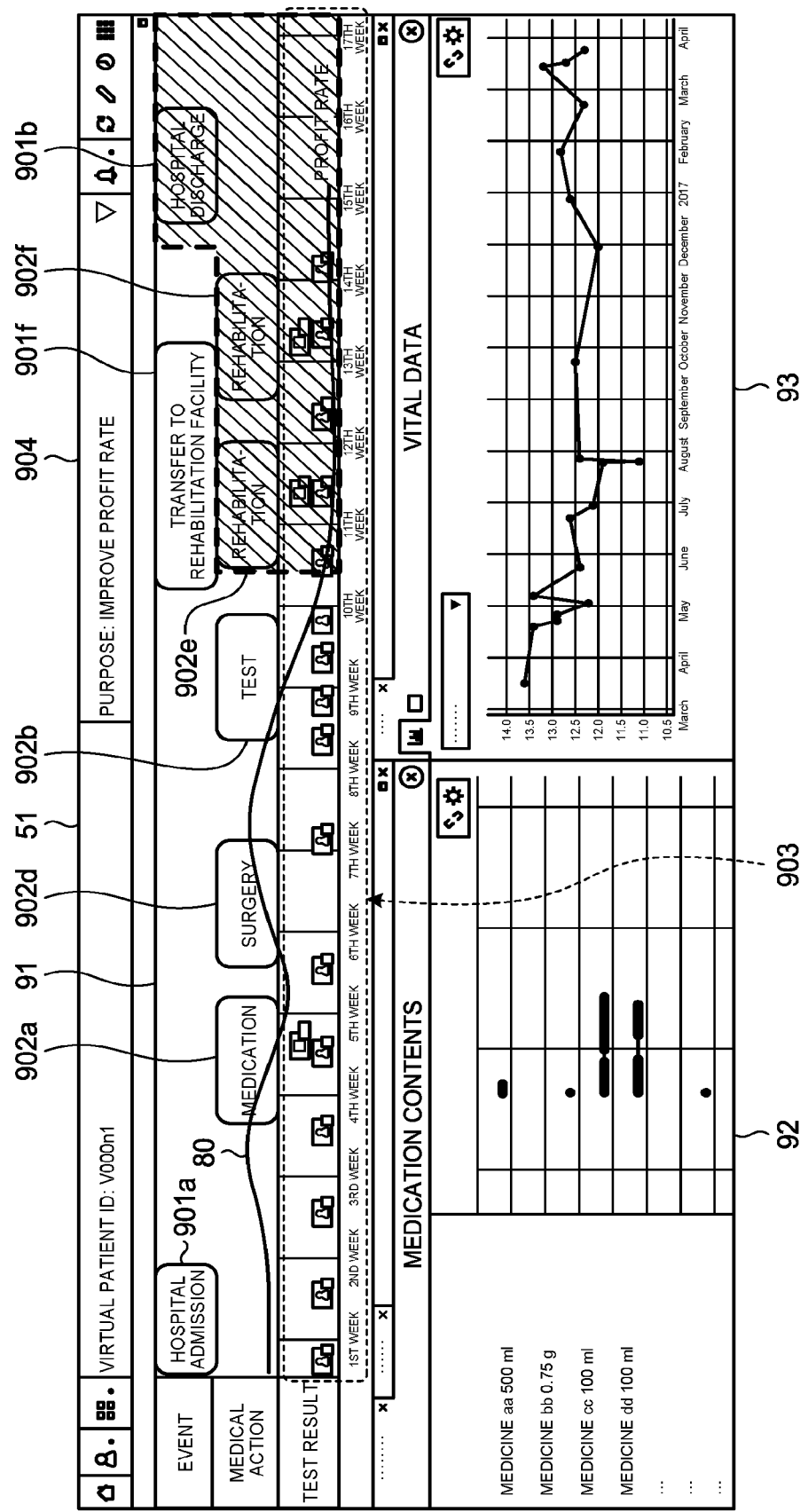
FIG. 12 is a view illustrating an example of a simulation screen according to a third embodiment.

FIG. 12 is a view illustrating an example of the simulation screen 51 according to the present embodiment. For example, when a purpose "improve a profit rate" is set as the simulation purpose as illustrated in FIG. 12, the display control function 153 displays a graph representing a time-series transition of the profit rate calculated by the simulation function 155 in the timeline box 91.

As illustrated in FIG. 12, the profit rate may decline during a rehabilitation period. In such a case, the operator may operate to add a new event "transfer to a rehabilitation facility" in the timeline box 91. The receiving function 154 receives the operation and sends the added event to the display control function 153 and the simulation function 155.

The simulation function 155 estimates a timing when the test result of the virtual patient model 71 satisfies the occurrence condition of the added event, and sets the estimated timing as the occurrence timing of the added event. The simulation function 155 also calculates a change in the financial index by the added event.

The display control function 153 displays the added event at a display position based on the occurrence timing of the event in the timeline box 91. The display control function 153 also grays out or deletes the event(s), the medical action(s), and the test result(s) that become unnecessary by adding the new event "transfer to a rehabilitation facility". The display control function 153 also changes the graph representing the time-series transition of the financial index in the timeline box 91 in accordance with the change in the financial index by the added event.

Additionally, the simulation function 155 may identify an event contributing to an improvement in the financial index based on the accounting information. The simulation function 155 may also identify a medical action contributing to an improvement in the financial index. In this case, the display control function 153 displays the event contributing to the improvement in the financial index as an addable event candidate. The display control function 153 may also display the medical action contributing to the improvement in the financial index in, for example, the medication content display box 92.

As described above, the medical information processing apparatus 100 according to the present embodiment displays, in the display 140, the financial index corresponding to the virtual patient model 71 displayed in the display 140. Thus, the medical information processing apparatus 100 according to the present embodiment enables a manager and others of a medical institution to easily execute the simulation for improving the financial index in addition to the advantageous effects of the first embodiment.

Modification 1

In the first to third embodiments as described above, "shorten a period from hospital admission to discharge", "avoid a death event", or "improve a profit rate" is listed as an example of the simulation purpose. The simulation purpose is not limited thereto. The simulation purpose may be, for example, "improve patient's quality of life (QOL)".

In the present modification, for example, medical actions that a doctor performs for a patient are classified into a medical action for purpose of cure of patient's disease and a medical action for purpose of improvement of patient's QOL. More particularly, if a medical action is "surgery", a surgery to remove a lesion area is "a surgery for purpose of cure of patient's disease". A surgery to mitigate patient's pain or discomfort is "a surgery for purpose of improvement of patient's QOL". If a medical action is "medication", a medication to reduce a lesion area or remove a virus, etc., causing the disease is "a medication for purpose of cure of patient's disease". A medication to mitigate patient's pain or discomfort is "a medication for purpose of improvement of patient's QOL".

When, for example, with the simulation screen 51, the operator sets the purpose "improve patient's QOL" as the simulation purpose, the display control function 153 may add a medical action for purpose of improvement of patient's QOL onto the timeline box 91

Alternatively, the display control function 153 may display, on the simulation screen 51, a list of medical actions that are classified into a medical action for purpose of improvement of patient's QOL and that are found to be effective to the case of the virtual patient displayed on the simulation screen 51. In this case, the receiving function 154 receives an operator's operation of selecting one or more medical actions from the list of the medical actions. The display control function 153 additionally displays the one or more medical actions selected by the operator on the timeline box 91.

Moreover, events for purpose of improvement of patient's QOL may be set for events. For example, "transfer to a hospice" is an example of the events for purpose of improvement of patient's QOL. When the operator sets the purpose "improve patient's QOL" as the simulation purpose, the display control function 153 may add an event "transfer to a hospice" onto the timeline box 91. The display control function 153 may change a type of event to be added in accordance with the case of the virtual patient.

Furthermore, the simulation function 155 determines whether "the medical action for purpose of improvement of patient's QOL" added or "the event for purpose of improvement of patient's QOL" added conflicts with the guidelines. When the simulation function 155 determines that the medical action or the event conflicts with the guidelines, the display control function 153 displays a warning on the display 140.

Moreover, the simulation function 155 determines whether, as a result of "the medical action for purpose of improvement of patient's QOL" added or "the event for purpose of improvement of patient's QOL" added, a change in the vital data, for example, exceeds a predetermined change amount. When the simulation function 155 determines that the change in the vital data exceeds the predetermined change amount, the display control function 153 displays a warning on the display 140.

Thus, the medical information processing apparatus 100 according to the present modification enables a doctor to easily execute a simulation for purpose of improvement of patient's QOL.

Modification 2

In the first to third embodiments as described above, the medical information processing apparatus 100 displays a result of simulation on the display 140; however, the method of outputting a result of simulation is not limited thereto. For example, the medical information processing apparatus 100 may send a result of simulation to an external device via a network. The processing circuitry 150 of the medical information processing apparatus 100 according to the present modification may include a sending function in addition to the acquisition function 151, the model generation function 152, the display control function 153, the receiving function 154, and the simulation function 155. The sending function is an example of a sender.

The acquisitor, the generator, the display controller, the receiver, and the simulator in the specification may be implemented by the processing circuitry 150 as described in the respective embodiments above. In addition, the same functions may be implemented by hardware only, software only, or mixture of hardware and software.

In accordance with at least one of the embodiments described above, a doctor and others can be assisted to examine or improve a process that a patient undergoes until reaching the final medical event.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical information processing apparatus comprising:
   processing circuitry; and
   a hardware display device, wherein
   the processing circuitry is configured to:
      generate a plurality of sets of virtual patient information in each of which patient attribute information, at least one medical action, at least one medical event, and at least one test result are associated with one another;
      receive a user's operation of selecting one of the sets of virtual patient information; and cause the hardware display device to display the event and the medical action included in the selected set of virtual patient information in time series, the hardware display device is configured to display, under control of the processing circuitry, the event and the medical action included in the selected piece of virtual patient information in time series, and the processing circuitry is further configured to:

receive a user's operation of selecting one from purpose items as a purpose for simulation, wherein the purpose items indicate a plurality of purposes including at least each of a shortening-of-hospitalization-period purpose and an improvement-in-profit-rate purpose, and the purpose items are pre-set;

change the event or the medical action displayed on the hardware display device based on the selected purpose item, correlation information, and an occurrence condition of the event, wherein the correlation information indicates a correlation between the medical action and the test result, and the occurrence condition indicates a condition of the test result defined by each combination of the event and an injury/disease name;

estimate a change in the test result of the set of virtual patient information displayed on the hardware display device in accordance with an operation of changing the medical action and the correlation information;

estimate a timing when the test result satisfies the occurrence condition as an occurrence timing of the event;

change a display position of the event displayed on the hardware display device in accordance with the occurrence timing estimated; and when it is determined that the change of the medical action conflicts with a guideline or when the change in the test result estimated in accordance with the change of the medical action possibly gives an adverse physiological effect on a patient, refuse the change of the medical action or cause the hardware display device to display a warning.

2. The medical information processing apparatus according to claim 1, wherein the processing circuitry is configured to:

determine whether a content of the medical action changed by the user's operation conflicts with a predetermined condition, and cause the hardware display device to display a warning when the content of the medical action changed by the user's operation is determined to conflict with the predetermined condition.

3. The medical information processing apparatus according to claim 2, wherein the processing circuitry is configured to:

determine whether the change in the test result based on the operation of changing the medical action exceeds a predetermined change amount, and cause the hardware display device to display a warning when the change in the test result is determined to exceed the predetermined change amount.

4. The medical information processing apparatus according to claim 1, wherein the processing circuitry is configured to:

receive a user's operation of adding a new event to the selected set of virtual patient information, estimate a timing when the test result included in the selected set of virtual patient information satisfies the occurrence condition as the occurrence timing of the added event, and display the added event at a display position based on the estimated occurrence timing.

5. The medical information processing apparatus according to claim 1, wherein the processing circuitry is configured to:

identify a medical action and a test result influencing the occurrence timing of the event related to the selected purpose item based on the correlation information and the occurrence condition, and cause the hardware display device to display the medical action and the test result identified as influencing the occurrence timing of the event.

6. The medical information processing apparatus according to claim 5, wherein the processing circuitry is configured to:

receive an operation of selecting, as the purpose, to change the last event included in the set of virtual patient information displayed on the hardware display device, and cause the hardware display device to display at least one different event substitutable for the last event as a substitutable event candidate.

7. The medical information processing apparatus according to claim 1, wherein the processing circuitry is configured to cause the hardware display device to display a financial index corresponding to the set of virtual patient information displayed on the hardware display device.

8. The medical information processing apparatus according to claim 1, wherein the event is hospital admission, hospital discharge, hospital transfer, or death, the patient attribute information is information in which an age, a gender, and an injury/disease name of a patient, and the last event occurring in connection with the patient in a medical institution are associated with each other, and the processing circuitry is configured to generate the virtual patient information based on medical record information having a common piece of the patient attribute information out of a plurality of sets of medical record information indicating records of medical actions actually given to a plurality of patients in the medical institution.

9. The medical information processing apparatus according to claim 1, wherein, in each of the plurality of virtual patient information, the at least one medical action is associated with at least one test result that is found to have a correlation with the at least one medical action.

10. The medical information processing apparatus according to claim 9, wherein the processing circuitry is configured to estimate the correlation between the at least one medical action and the at least one test result based on at least a temporal relation between a time corresponding to the at least one medical action and a time corresponding to the at least one test result.

* * * * *